(12) United States Patent
Durand et al.

(10) Patent No.: US 6,520,941 B1
(45) Date of Patent: Feb. 18, 2003

(54) METHOD AND DEVICE FOR ENTRAPPING GAS WITHIN A LIQUID DRUG CONTAINER

(76) Inventors: Kevin Durand, 13 Massachusetts Ave., Harvard, MA (US) 01451; Izrail Tsals, 17 Rose Way, Sudbury, MA (US) 01776; Craig Brodeur, 26 Dalton Rd., Marlborough, MA (US) 01752

( * ) Notice: Subject to any disclaimer, the term of this patent is extended or adjusted under 35 U.S.C. 154(b) by 0 days.

(21) Appl. No.: 09/415,961

(22) Filed: Oct. 12, 1999

Related U.S. Application Data

(60) Provisional application No. 60/103,586, filed on Oct. 9, 1998.

(51) Int. Cl.[7] ............................. A61M 5/14; B65D 39/02
(52) U.S. Cl. ........................ 604/256; 604/415; 215/247
(58) Field of Search .................... 215/247; 210/516, 210/518; 604/256, 257, 403, 415, 905; 600/573, 578

(56) References Cited

U.S. PATENT DOCUMENTS

| | | | |
|---|---|---|---|
| 3,916,894 A | | 11/1975 | Cloyd |
| 4,568,336 A | | 2/1986 | Cooper |
| 5,361,921 A | * | 11/1994 | Burns .................... 215/247 X |
| 5,632,396 A | * | 5/1997 | Burns ........................ 215/247 |
| 5,632,895 A | * | 5/1997 | Tsukagoshi et al. ........ 210/518 |

FOREIGN PATENT DOCUMENTS

| WO | WO 97/14460 | 4/1997 |
|---|---|---|

* cited by examiner

*Primary Examiner*—Anhtuan T. Nguyen
(74) *Attorney, Agent, or Firm*—Caesar, Rivise, Bernstein, Cohen & Pokotilow, Ltd.

(57) ABSTRACT

A stopper for use in preventing any volume of gas from escaping from a drug container when used in connection therewith. The stopper has a body having a perimeter for slidable engagement with the interior of a drug receptacle; an outer surface; and an inner surface facing the bottom of the drug receptacle, the inner surface shaped so as to trap any volume of gas located within the drug receptacle when the body is slidably engaged therein. The invention is further directed to a drug container having a hollow body for holding a liquid. The body has an open end and a closed end. The container also has a stopper slidably received in the hollow body, and a feature for entrapping any volume of gas within the container.

10 Claims, 6 Drawing Sheets

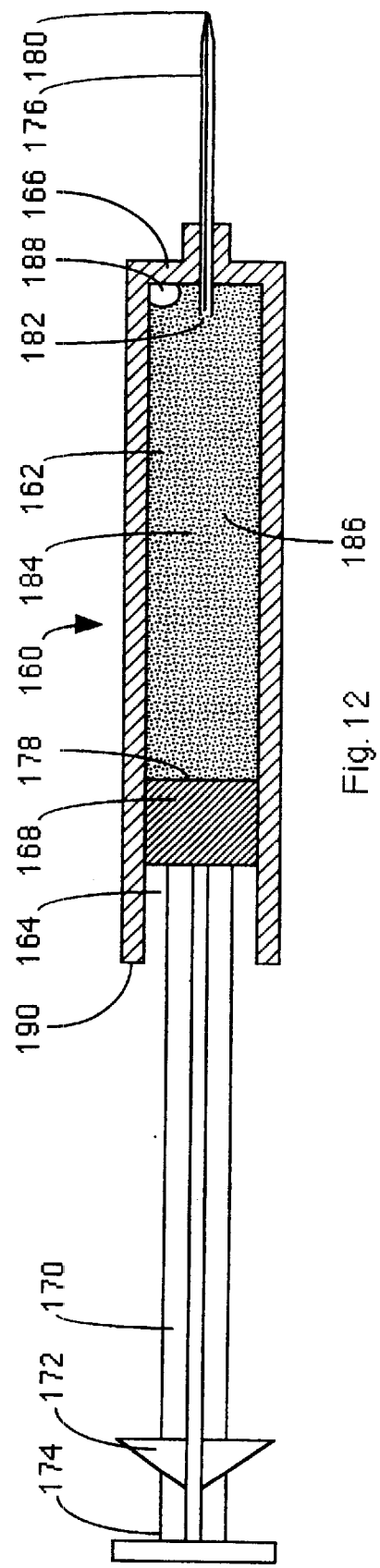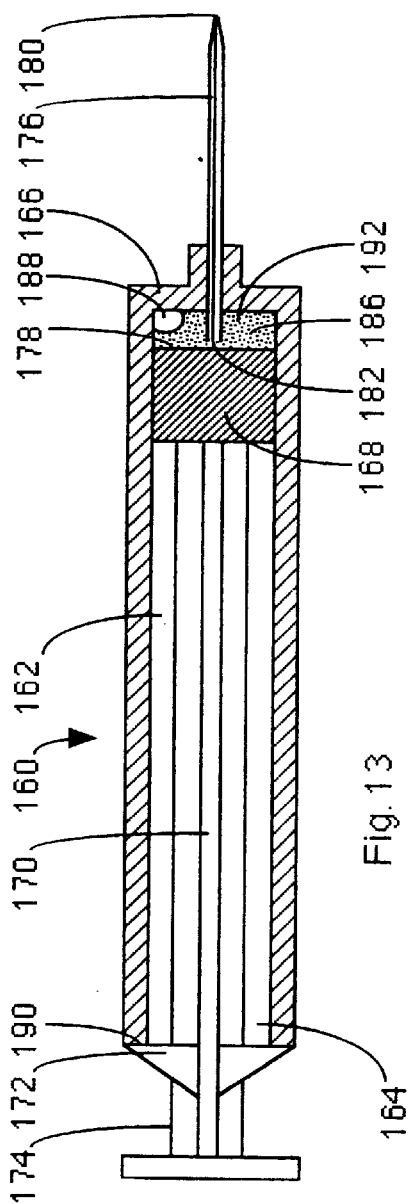
Fig. 12
Fig. 13

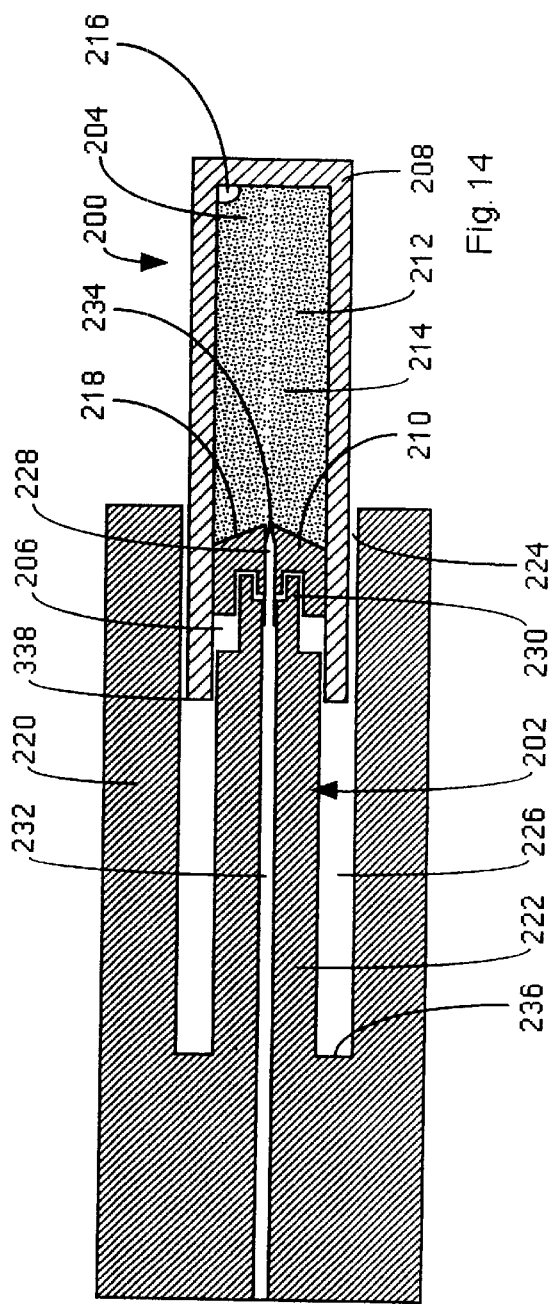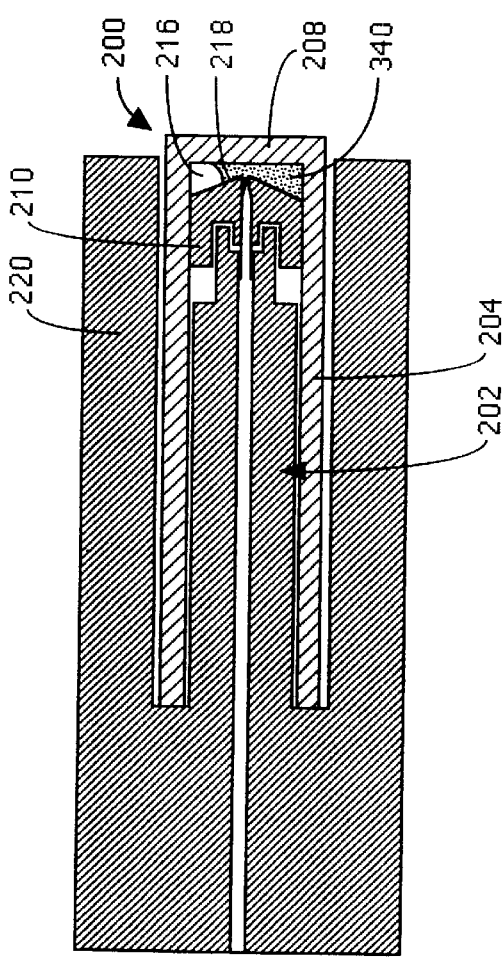

METHOD AND DEVICE FOR ENTRAPPING GAS WITHIN A LIQUID DRUG CONTAINER

This application claims the benefit of provisional application No. 60/103,586, filed Oct. 9, 1998.

TECHNICAL FIELD

The present invention relates to devices and methods for entrapping gas in liquid drug containers, and in particular relates to drug cartridges and stoppers for filling drug delivery devices, and methods relating to such filling.

BACKGROUND OF THE INVENTION

For reasons of stability and accuracy of delivery it is often desired to store a liquid drug in a container such as a standard drug cartridge. Such cartridges may typically be cylindrical and be sealed at an open end by a penetrable stopper or piston. To release the drug, the stopper is typically punctured by a hollow needle and then moved along the length of the container whereupon it acts as a piston to pump liquid drug from the container through the needle. Such cartridges are typically used in pre-filled syringes of the type manufactured by IMS of So. El Monte, Calif., U.S.A. and by Abbott Laboratories of N. Chicago, Ill., U.S.A. and also in the infusion system, which is the subject of WO 95/13838.

If any air or gas is present in the cartridge after it is sealed with the stopper, then air or gas may be transferred from the cartridge with the drug. For systems applied by trained personnel (e.g. nurses and doctors) the air can be eliminated through appropriate orientation. However when such systems are used by patients and untrained caregivers there is a danger that the safety may be affected. There are several safety risks associated with air bubbles getting into an infusion pump, syringe or the like. For example, if there is a volume of air delivered via a drug delivery device, then all of the prescribed volume of drug may not be delivered.

Overall accuracy of drug delivery may also be affected when air or other gas is transferred into a drug delivery system. If some of the drug cartridge volume is taken up by air or gas rather than liquid drug, then the prescribed amount of liquid drug is not being delivered to the patient. In cases where the drug being delivered has a narrow therapeutic window, if that window is exceeded due to an air bubble obstruction in the pathway of the drug delivery device, exceeding the window may result in undesirable deleterious side effects. Drugs in this category include aminoglycosides such as Amikacin, Gentamicin, Kanamycin and tobramycin.

In addition to the problem of air bubble obstruction, a volume of air or gas in the drug cartridge may result in a decreased volume of drug delivered. Patients that require drugs that have extremely accurate dosing regimes may suffer if the volume of drug delivered is inaccurate due to the excess volume of gas in the cartridge. Pediatric and geriatric patient groups are typically more sensitive to such dose administrations.

If the drug is a painkiller, such as morphine, extreme suffering will be caused to the patient due to a cessation of drug delivery. In addition, in the case of intravenous delivery, air bubbles may pass into the user's blood system and obstruct blood flow, thereby causing serious injury and possibly death.

Experience has shown that the manufacturers and fillers of drug cartridges are unable to eliminate air or other gas entirely from their drug cartridges, and for a relatively small volume (5 ml) cartridge, it has not been possible to reduce the amount of air or other gas present to below 25 $\mu$l. Typical volumes of gas are in the 100 to 300 $\mu$l range.

Moreover, most drug cartridges are filled under sterile conditions and via automatic machinery. Thus, any improvement to the standard drug cartridge that would entrap gas therein and prevent from passing through to a drug delivery device must be able to comply with existing filling and assembly machinery presently used in the industry.

Thus, there is a need for a drug cartridge assembly that entraps gas therein and prevents it from being transferred with liquid drug to a drug delivery device.

There is a further need for a drug cartridge assembly that increases patient safety by preventing any gas from being transferred to a drug delivery device.

There is still a further need for a drug cartridge assembly that increases dosage accuracy in liquid drug delivery via a drug delivery device by preventing any gas from being transferred to such drug delivery device.

There is yet a further need for a stopper that can be used in connection with a standard drug cartridge that entraps gas between the drug cartridge and stopper and prevents it from being transferred with liquid drug to a drug delivery device.

There is a further need for a stopper used in connection with a standard drug cartridge that increases patient safety by preventing any gas transferred from the cartridge to a drug delivery device.

There is still a further need for a stopper used in connection with a standard drug cartridge that increases dosage accuracy in liquid drug delivery via a drug delivery device by preventing any gas from being transferred from the drug cartridge to such drug delivery device.

There is a further need for a method for entrapping gas within a liquid drug container that prevents such gas from being transferred with liquid drug to a drug delivery device.

There is yet a further need for a stopper, used in connection with a standard drug cartridge that prevents gas from being transferred to a drug delivery device, designed for use in presently existing filling and assembly machinery.

There is still a further need for a drug cartridge that prevents gas from being transferred to a drug delivery device, designed for use in presently existing filling and assembly machinery.

SUMMARY OF THE INVENTION

The present invention solves the problems associated with the prior art devices and methods by providing for a stopper for use in preventing any volume of gas from escaping from a drug container when used in connection therewith. The stopper comprises a body having a perimeter for slidable engagement with the interior of a drug receptacle, an outer surface, and an inner surface facing the bottom of the drug receptacle. The inner surface is shaped so as to trap any volume of gas located within the drug receptacle when the body is slidably engaged therein.

Such geometries of stopper and/or container create a natural space to trap any gas away from the outlet, as will be described in further detail below.

The inner surface of the stopper is preferably convex, and in particular may be conical, or frusto-conical. The body of the stopper is preferably circular in cross-section.

The stopper may further include an outlet. The outlet connects the inner surface with the outer surface. The outlet is preferably aligned along the longitudinal axis of the stopper. The outlet may be created by penetrating the stopper. The outlet may comprises a hollow needle extending through the inner and outer surfaces of the stopper. This helps ensure sterility of the liquid drug by preventing any interference with the drug between the filling of the container and the emptying thereof.

A second embodiment of the present invention is directed to a liquid drug container. The container includes a hollow body for holding a liquid. The body has an open end and a closed end. The container also includes a stopper slidably received in the hollow body, and means for entrapping a predetermined volume of gas within the container.

Preferably, the hollow body is substantially cylindrical in form and the stopper is of substantially circular cross-section to make a sealing sliding fit with the internal bore of the cylindrical hollow body.

Suitably, the means for preventing exit of gas and entrapping the gas comprises a convex, conical or frusto-conical liquid-facing surface provided on the stopper. Preferably, the entrapping means is located along the perimeter of the stopper. Alternatively, the means for preventing exit of gas and entrapping the gas comprises a convex, conical or frustoconical surface provided on an internal end surface of the substantially cylindrical hollow body facing the stopper.

The container may further include an outlet associated with the stopper through which drug is expelled. Preferably, the outlet is located along the central longitudinal axis of the stopper. For example, the outlet can be a narrow axial bore having a needle or a conduit extending therefrom. Preferably, in such cases, the outlet is created in use by penetrating the stopper. This helps ensure sterility of the liquid drug by preventing any interference with the drug between the filling of the container and the emptying thereof.

When the stopper has slidably moved to the closed end of the hollow body, the gas volume in the container is entrapped away from the outlet. The container is designed to prevent any volume of gas from exiting through the outlet and the gas is entrapped within the container regardless of orientation of the body. Preferably, the outlet is sealed when the stopper reaches the limit of its travel.

The container may further include means for limiting the travel of the stopper. Such means may be external to the hollow body. The container may also include means for slidably moving the stopper within the hollow body. The container may further include means for limiting the travel of the stopper. Such means may be made up of co-operating surfaces on the hollow body and on the means for slidaby moving the stopper within the hollow body.

In further preferred embodiments, the outlet comprises a needle extending partially into the interior of the container through a wall of the container facing the stopper, so as to provide the means for preventing exit of gas and entrapping the gas in the container, the needle limiting the travel of the stopper, thereby forming the entrapment space. The needle may enter the hollow body through either the stopper or a wall of the hollow body.

The present invention is also directed to a position independent method of emptying a liquid drug container while retaining any volume of gas within the container. The method includes the steps of providing a hollow body having an open end and a closed end, the body having liquid drug contained therein, closing the open end of the body with a stopper slidably received within the hollow body at the open end to prevent liquid drug from escaping therefrom. The method further includes the steps of creating an outlet through the longitudinal axis of the stopper through which the liquid drug may be expelled, providing a space between the stopper and the closed end of the body for occupation by any volume of gas within the body, moving the stopper from the open end to the closed end of the body, thereby causing the volume of liquid drug to be expelled from the body via the outlet and, when the stopper completes its travel to the closed end of the hollow body, forcing any volume of gas remaining therein to be located in the space thus preventing the volume of gas from escaping from the body via the outlet.

The step of moving the stopper may be accomplished by causing the stopper to slide along its longitudinal axis within the hollow body. The outlet may be created by extending a hollow needle through the stopper and into the interior of the container.

The use of a volume of gas or an gas trap has been found to eliminate problems associated with the transfer of residual gas trapped in drug containers. It ensures that a small and possibly variable amount of gas, which may become entrapped during the filling process (which in fact is practically impossible to avoid), is never ejected because the container is designed to retain a small amount of liquid drug which would include any entrapped gas when the container is essentially empty. Accordingly, containers according to the invention are designed to ensure that only liquid is expelled by movement of the stopper, and because the dimensions of the stopper and the hollow body can be precisely controlled, it is possible to ensure highly accurate delivery volumes.

This design of container allows the container to be used (e.g. in filling a portable infusion pump) by persons having no training. Whereas a certain degree of training and experience is required to prevent gas contained in a syringe from being transferred to the patient's tissue or bloodstream. The container according to the invention automatically traps and retains the gas away from the outlet.

The design of the container and of the stopper are also conducive for use with existing automated filling machinery. The stopper and container of the present invention are of the proper exterior dimensions for use in connection with presently available filling and assembly equipment. Thus, there is no need for any retro-fitting or replacement of such machinery.

Other objects, features and advantages of the present invention will become apparent upon reading the following detailed description of the embodiments of the invention when taken in conjunction with the drawings and the appended claims.

BRIEF DESCRIPTION OF THE DRAWINGS

FIG. 12 is a cross-sectional side view of a sixth preferred embodiment of a liquid drug container according to the present invention;

FIG. 13 is a cross-sectional side view of the container of FIG. 12, after the container is emptied;

FIG. 14 is a cross-sectional side view of a seventh preferred embodiment of a liquid drug container according to the present invention engaged with a drug loading mechanism prior to emptying of the container; and FIG. 15 is a cross-sectional side view of the container of FIG. 14 engaged with a drug loading mechanism following emptying of the container.

DETAILED DESCRIPTION OF THE INVENTION

Figure 1:
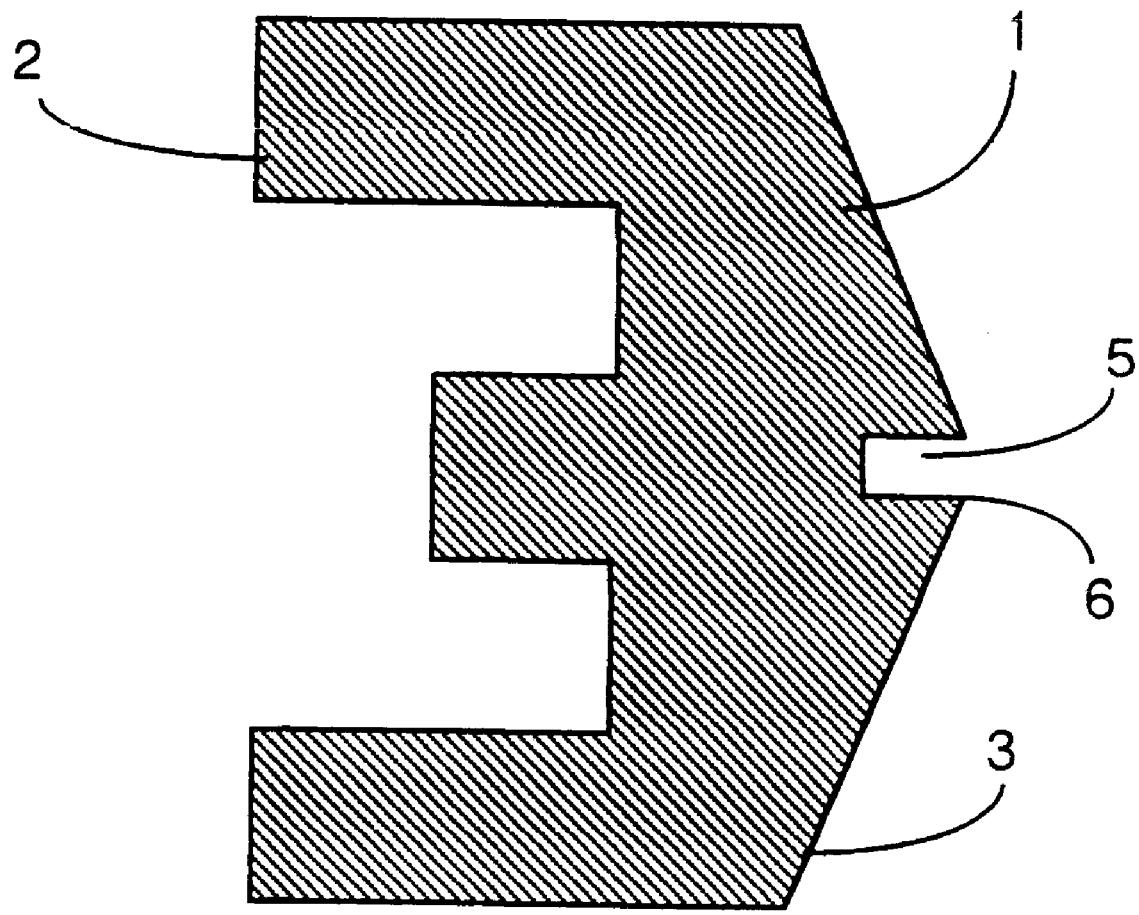
FIG. 1 is a cross-sectional side view of a first preferred embodiment of the stopper of the present invention.

Referring now in more detail to the drawings in which like numerals refer to like parts throughout the several views, FIG. 1 shows a stopper 1 having an outer surface 2 and an inner surface 3. The outer surface 2 is exposed to the atmosphere when inserted in a drug container (not shown). The stopper 1 is circular in cross-section and designed to sliding fit within a drug container. The inner surface 3 is convex in shape and has a partial channel inlet 5 at the tip 6 of the convex inner surface. The channel inlet 5 is located along the central longitudinal axis of the stopper 1. The stopper is typically made of a rubber or polymer material to provide such a sliding fit. The preferred material of the stopper is butyl.

The channel inlet provides for effective transfer of liquid drug from the container as explained in more detail below. The length of most needles used in connection with a stopper of the present invention is limited. Thus, the channel inlet provides clearance for the needle after a relatively short length of travel through the stopper.

Figure 2:
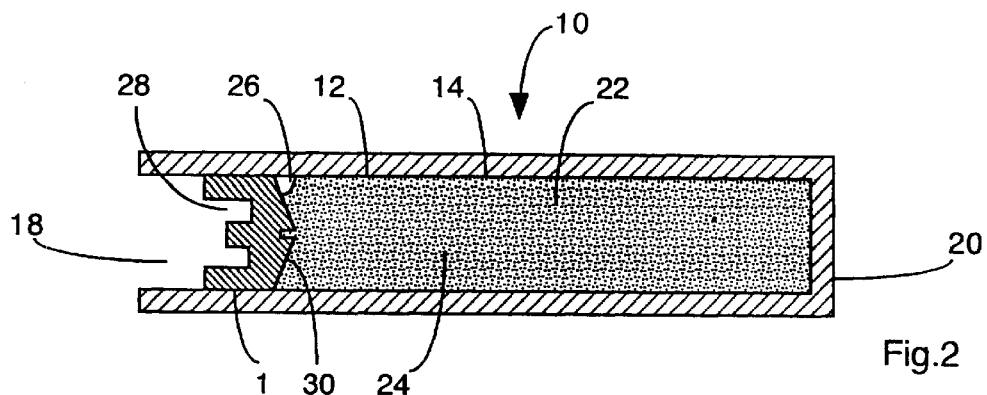
FIG. 2 is a cross-sectional side view of a second preferred embodiment of the liquid drug container of the present invention.

FIG. 2 shows a second preferred embodiment 10 of present invention. The second embodiment 10 comprised a container 12 having comprises a hollow body 14 and a stopper 1. The hollow body 14 is in the form of a cylindrical glass tube open at one end 18 and closed at the other end 20. The stopper 1 is slidably received in the hollow body 14 to define a sealed internal chamber 22 containing a liquid drug 24. A small air bubble 26 resulting from the filling process is also present. The outer surface 2 of the stopper 1 has an annular recess 28 and the inner surface 3 has a sloping frusto-conical face 30 with the partial channel inlet 5 located at the tip 6 of the face, as shown in part in FIG. 1.

Figure 3:
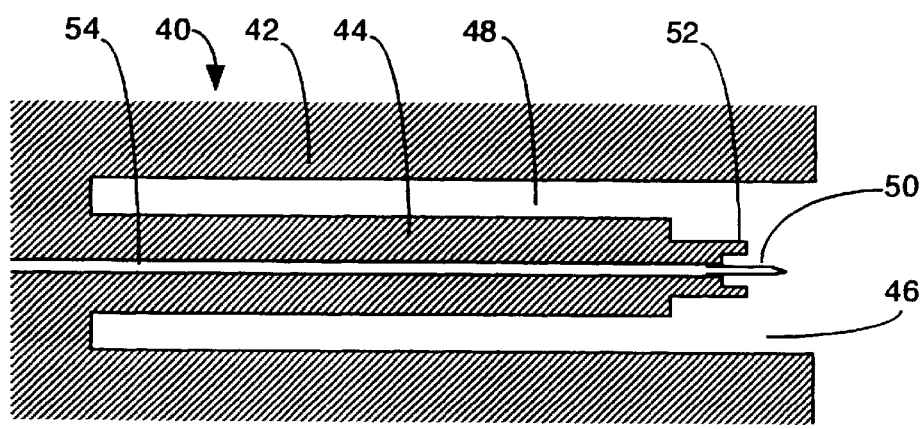
FIG. 3 is a detailed cross-sectional side view of a drug loading mechanism for receiving and emptying the container of FIG. 2.

FIG. 3 shows a drug loading mechanism, indicated generally at 40, for receiving and emptying the container of FIG. 2. The mechanism 40 is of a type which might be integral with a housing 42 of an infusion system having a reservoir and a pumping means for pumping a liquid drug from the reservoir. The mechanism 40 could also be integral with a syringe of an infusion system. The mechanism 40 is formed in the housing 42 of an infusion system and comprises a cylindrical finger 44 extending axially within a cylindrical bore 46 formed in the housing to create an annular gap 48 along a portion of the length of the mechanism.

Figure 4:
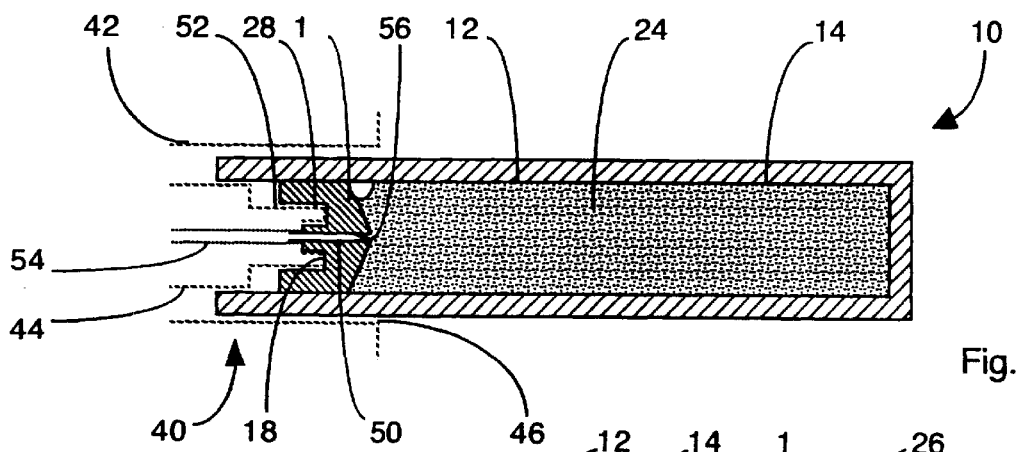
FIG. 4 is a detailed cross-sectional side view of the container of FIG. 2 when mounted on the mechanism of FIG. 3, before the container is emptied.

A needle 50 is mounted on an end 52 of the cylindrical finger 44 and creates an interference fit with the outer surface of one end of a central channel 54. The central channel 54 is located along the central axis of the cylindrical finger 44 and leads to the reservoir (not shown) of the infusion pump. Referring additionally to FIG. 4, for clarity, the housing 42, cylindrical finger 44 and central channel 54 can be partially seen in phantom.

In use, the container 12 is received into the bore 46 of the mechanism 40 (FIG. 4), causing the annular recess 28 of the stopper 1 to abut against the end 52 of the cylindrical finger 44, and also causing the needle 50 to penetrate into and through the stopper 1, as shown, so that tip 56 of the needle 50 is in communication with the liquid drug 24 within the hollow body 14.

To empty the container 12, the hollow body 14 is simply pushed further into the bore 46. Because the stopper 1 abuts against the end 52 of the cylindrical finger 44, and the needle 50 has penetrated into and through the stopper, the container 12 is forced to empty by the movement of the stopper towards the closed end 20 of the hollow body 14, with the liquid drug 24 being pumped through the needle 50 via the central channel 54 to the reservoir.

Figure 5:
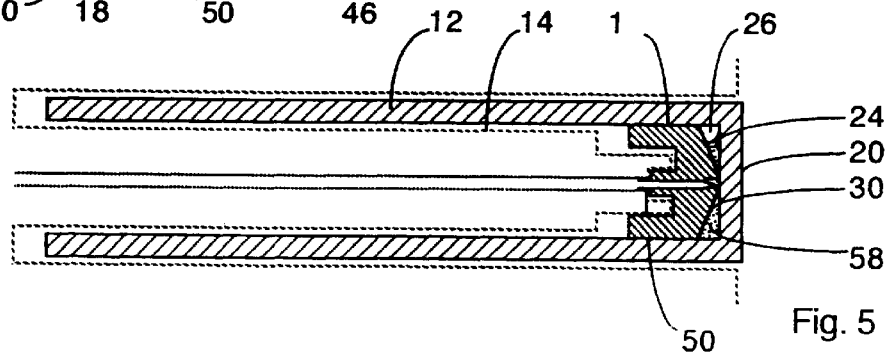
FIG. 5 is a cross-sectional side view of the container of FIG. 2 when mounted on the mechanism of FIG. 3, after the container is emptied.

FIG. 5 shows the container 12 when it has been emptied of the liquid drug 24, i.e. when the stopper 1 has been pushed against the closed end 20 of the hollow body 14. The frusto-conical face 30 of the stopper 1 creates a space 58 adjacent to the interior of the closed end 20, entrapping the air bubble 26 along with a small volume of the liquid drug 24. The invention is particularly adapted for use with containers having a filled volume of not greater than about 20 ml, more preferably not greater than about 10 ml, 5 ml or 1 ml.

Figure 6:
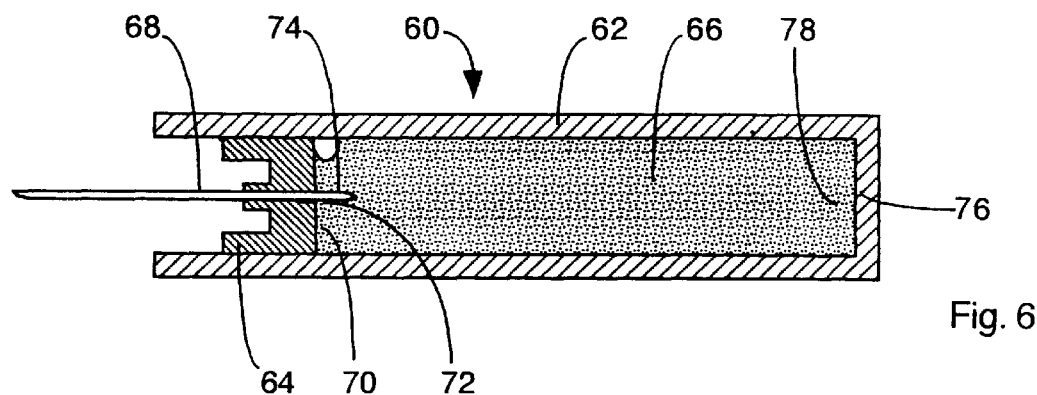
FIG. 6 is a cross-sectional side view of a third preferred embodiment of a liquid drug container according to the present invention.

In FIG. 6 there is illustrated a second preferred embodiment of the liquid drug container according to the invention indicated generally at 60. The container 60, like container 12 in FIGS. 2–5, also comprises a hollow body 62 and a stopper 64. It too is therefore in the form of a liquid drug container from which liquid drug is released by penetrating the stopper 64 and using the stopper 64 as a piston to pump a liquid drug 66 from the interior of the hollow body 62. For simplicity, the mechanism for emptying the container 60 is not shown, apart from a needle 68 which is penetrating the stopper 64. Nevertheless, the container 60 is emptied in identical manner to that described in relation to container 12 (FIGS. 2–5).

The container 60 differs from the container 12 (FIGS. 2–5) in that liquid-facing surface 70 of the stopper 64 is substantially flat (apart from a small recess 72 from which the tip 74 of the needle 68 protrudes in use) rather than frusto-conical. Closed end 76 of the hollow body 62 is also flat on its internal end surface 78.

Figure 7:
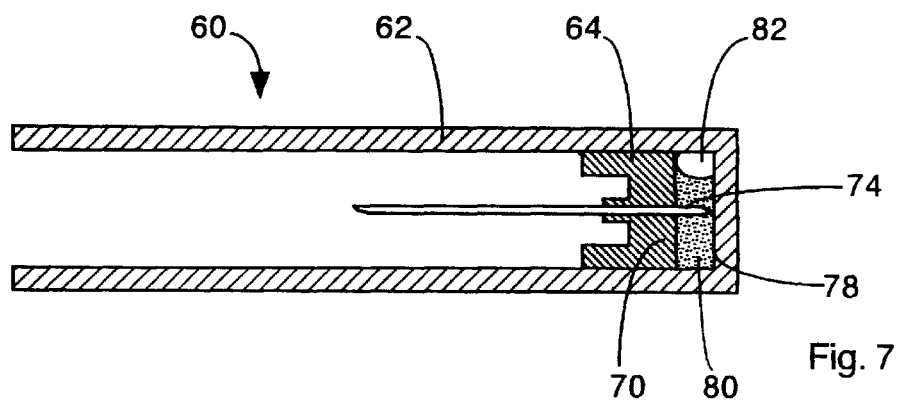
FIG. 7 is a cross-sectional side view of the container of FIG. 6, after the container is emptied.

Referring to FIG. 7, it can be seen that when the stopper 64 has reached the end of its travel within the hollow body 62, thereby effectively emptying the container 60, a space 80 remains between the internal end surface 78 of the hollow body 62 and the liquid-facing surface 70 of the stopper 64. A small known volume of fluid (comprising liquid drug 66 and an air bubble 82) is thus entrapped in this space 80.

Figure 8:
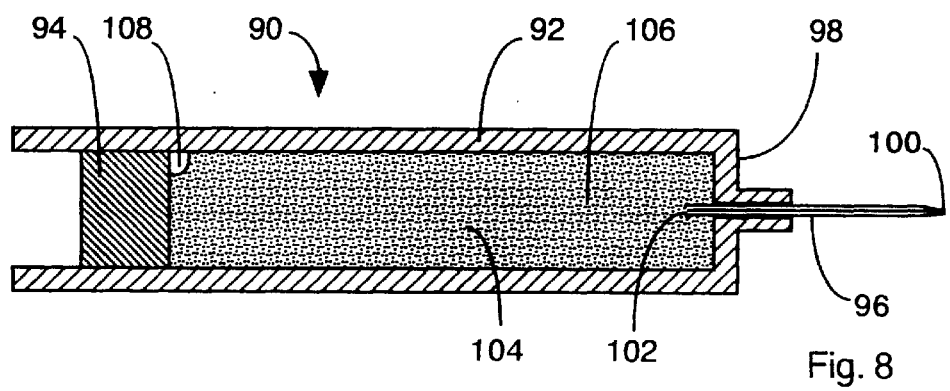
FIG. 8 is a cross-sectional side view of a fourth preferred embodiment of a liquid drug container according to the present invention.

In FIG. 8 there is illustrated a third preferred embodiment of the container according to the present invention indicated generally at 90. Like the previously described embodiments, the container 90 comprises a hollow body 92 and a stopper 94 slidably mounted therein. However, in the case of the container 90, the outlet of the container 90 is provided as a hollow needle 96 mounted in closed end 98 of the hollow body 92, such that the container 90 is in the form of a syringe rather than a drug cartridge.

The needle 96 is mounted with an outer end 100 outside the hollow body 92 and an inner end 102 protruding into the hollow body 92. An internal chamber 104 is defined by the stopper 94 and the interior of the hollow body 92 and this internal chamber 104 is filled with a liquid drug 106 containing an air bubble 108.

Figure 9:
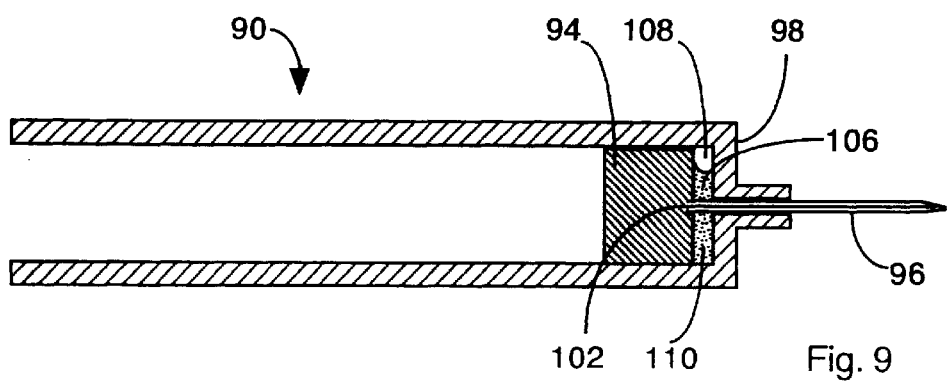
FIG. 9 is a cross-sectional side view of the container of FIG. 8, after the container is emptied.

The liquid drug 106 is ejected as from a conventional syringe by depressing a plunger (not shown) to slide the stopper 94 within the hollow body 92 and thereby eject the liquid drug 106 via the needle 96. However, when the internal chamber 104 has been substantially emptied of the liquid drug 106 (as shown in FIG. 9), the stopper 94 reaches the limit of its travel by meeting the inner end 102 of the needle 96. This provides a means for retaining a known volume of fluid in the container 90 because a space 110 remains in which a small volume of the liquid drug 106 and the air bubble 108 are entrapped. Thus, the air bubble 108 is not injected into the patient via the needle 96 as would be the case with a conventional syringe. This makes the container 90 more suitable for use by untrained personnel than conventional syringes which must be carefully freed of any air bubbles before injection occurs.

Figure 10:
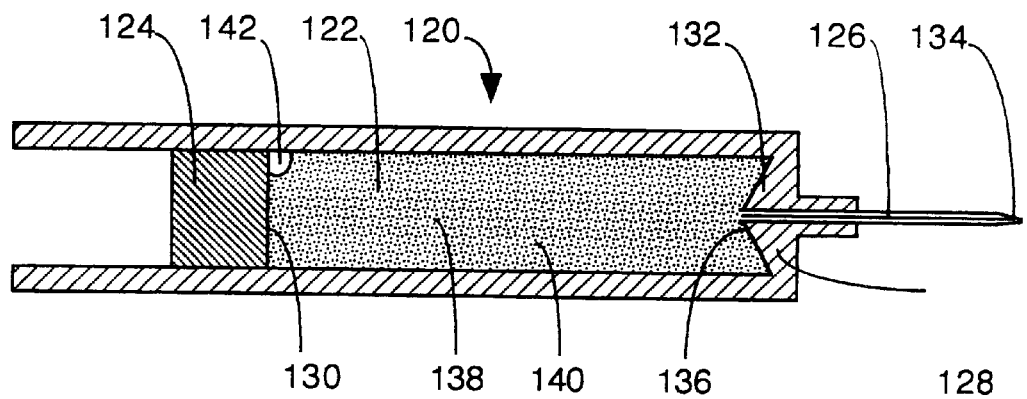
FIG. 10 is a cross-sectional side view of a fifth preferred embodiment of a liquid drug container according to the present invention.
Figure 11:
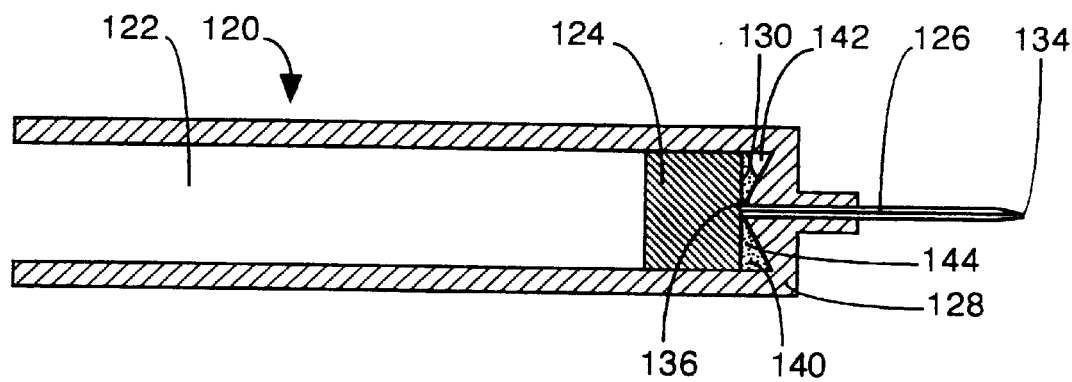
FIG. 11 is a cross-sectional side view of the container of FIG. 10, after the container is emptied.

In FIG. 10 there is illustrated a fourth embodiment of the container according to the invention indicated generally at 120. As with the previously described embodiments, the container 120 comprises a hollow body 122 and a stopper 124 slidably mounted therein. As in the case of the embodiment of FIGS. 8 and 9, the outlet of the container 120 is provided as a hollow needle 126 mounted in closed end 128 of the hollow body 122, such that the container 120 is in the form of a syringe. Liquid facing surface 130 of the stopper 124 is substantially flat and closed end 128 of the container has a conical surface 132. The needle 126 is mounted with an outer end 134 outside the hollow body 122 and an inner end 136 which communicates with the hollow body but does not extend beyond conical surface 132. An internal chamber 138 is defined by the stopper 124 and the interior of the hollow body 122. The internal chamber 138 is filled with liquid drug 140 containing an air bubble 142. The liquid drug 140 is ejected from the container 120 in the same manner as for the embodiment of FIGS. 8 and 9. Thus, the stopper 124 reaches the limit of its travel by meeting the inner end 136 of the needle 126, thereby providing a space 144 in which a small volume of the liquid drug 140 and the air bubble 142 are entrapped (as shown in FIG. 11).

Referring to FIG. 12, there is illustrated a fifth embodiment of a container according to the invention indicated generally at 160. The container 160 comprises a hollow body 162 having an open end 164 and a closed end 166 and a stopper 168 slidably mounted therein. The stopper 168 is actuated by a plunger 170 having an annular flange 172 at its end 174 remote from the stopper 168. As in the case of the embodiments of FIGS. 8 and 9 and FIGS. 10 and 11, the outlet of the container 160 is provided as a hollow needle 176 mounted in closed end 166 of the hollow body 162, such that the container 160 is in the form of a syringe. Liquid facing surface 178 on the stopper 168 is substantially flat as is closed end 166. Needle 176 is mounted with an outer end 180 outside of the hollow body 162 and an inner end 182 protruding into said hollow body. An internal chamber 184 is defined by the stopper 168 and the interior of the hollow body 162. The internal chamber 184 is filled with liquid drug 186 containing an air bubble 188. The liquid drug 186 is ejected from the container 160 when the plunger 170 is depressed. The stopper 168 reaches the limit of its travel when the flange 172 encounters and abuts wall 190 at the open end 164 of the container 160. A space 192 is created between the surface 178 and the closed end 166 in which a small volume of liquid drug 186 and the air bubble 188 are entrapped as shown in FIG. 13. It will be appreciated that the positioning of the flange 172 will determine the volume of the space created.

Referring to FIG. 14, there is illustrated a sixth embodiment of a container according to the invention indicated generally at 200 engaging a drug loading mechanism indicated generally at 202 for receiving and emptying the container 200. The container 200 comprises a hollow body 204 having an open end 206 and a closed end 208 and a stopper 210 slidably mounted therein to define a sealed chamber 212 containing a liquid drug 214 and an air bubble 216, resulting from the filling process. Liquid facing surface 218 of the stopper 210 is substantially conical and the closed end 208 of the hollow body 204 is substantially flat. As in the case of the embodiment illustrated in FIGS. 2–5, the drug loading mechanism 202 is of a type which might be integral with a housing 220 of an infusion system having a reservoir and a pumping means (not shown) for pumping a liquid drug from the reservoir. The mechanism 202 is formed in the housing 220 of such an infusion system and comprises a cylindrical finger 222 extending axially within a cylindrical bore 224 to create an annular gap 226 along a portion of the length of the mechanism 202.

A needle 228 is mounted on an end 230 of the cylindrical finger 222 and creates an interference fit with the outer surface of one end of a central channel 232. The central channel 232 is located along the central axis of the cylindrical figure 222 and leads to the reservoir of the infusion pump In use, and as illustrated in FIGS. 14 and 15, the container 200 is received into the cylindrical bore 224 of the mechanism 202, causing the stopper 210 to abut against the end 230 of the cylindrical finger 222 and also causing the needle 228 to penetrate into and through the stopper 210 as shown, so that tip 234 of the needle 228 is in communication with the liquid drug 214 within the hollow body 204.

To empty the container 200, the hollow body 204 is pushed further into the bore 224 (relative to the position shown in FIG. 14) and is emptied in the manner described in relation to FIGS. 2–5, except that the stopper 210 reaches the limit of its travel when end 236 of the central bore 224 encounters and abuts wall 338 at the open end 206 of the container 200.

FIG. 14 shows the container 200 when it has been emptied of the liquid drug 214. A dead space 340 is created between surface 218 of stopper 210 and closed end 208 of the container 204 in which a small volume of the liquid drug 214 and the air bubble 216 are entrapped. It will be appreciated that the length of central bore 224 will determine the volume of the dead space created.

It is further appreciated that the present invention may be used to deliver a number of drugs. The term "drug" used herein includes but is not limited to peptides or proteins (and mimetic thereof), antigens, vaccines, hormones, analgesics, anti-migraine agents, anti-coagulant agents, medications directed to the treatment of diseases and conditions of the central nervous system, narcotic antagonists, immunosuppressants, agents used in the treatment of AIDS, chelating agents, anti-anginal agents, chemotherapy agents, sedatives, anti-neoplastics, prostaglandins, antidiuretic agents and DNA or DNA/RNA molecules to support gene therapy.

Typical drugs include peptides, proteins or hormones (or any mimetic or analogues of any thereof) such as insulin, calcitonin, calcitonin gene regulating protein, atrial natriuretic protein, colony stimulating factor, betaseron, erythropoietin (EPO), interferons such as α, β or γ interferon, somatropin, somatotropin, somastostatin, insulin-like growth factor (somatomedins), luteinizing hormone releasing hormone (LHRH), tissue plasminogen activator (TPA), growth hormone releasing hormone (GHRH), oxytocin, estradiol, growth hormones, leuprolide acetate, factor VIII, interleukins such as interleukin-2, and analogues or antagonists thereof, such as IL-1ra; analgesics such as fentanyl, sufentanil, butorphanol, buprenorphine, levorphanol, morphine, hydromorphone, hydrocodone, oxymorphone, methadone, lidocaine, bupivacaine, diclofenac, naproxen, paverin, and analogues thereof; anti-migraine agents such as sumatriptan, ergot alkaloids, and analogues thereof; anti-coagulant agents such as heparin, hirudin, and analogues thereof; anti-emetic agents such as scopolamine, ondansetron, domperidone, metoclopramide, and analogues thereof; cardiovascular agents, anti-hypertensive agents and vasodilators such as diltiazem, clonidine, nifedipine, verapamil, isosorbide-5-mononitrate, organic nitrates, agents used in treatment of heart disorders, and analogues thereof; sedatives such as benzodiazepines, phenothiazines, and analogues thereof; chelating agents such as deferoxamine, and analogues thereof; antidiuretic agents such as desmopressin, vasopressin, and analogues thereof; anti-anginal agents such as nitroglycerine, and analogues thereof; anti-neoplastics such as fluorouracil, bleomycin, and analogues thereof; prostaglandins and analogues thereof; and chemotherapy agents such as vincristine, and analogues thereof, treatments for attention deficit disorder, methylphenidate, fluvoxamine, bisoprolol, tacrolimus, sacrolimus and cyclosporin.

It will be appreciated that the embodiments discussed above are preferred embodiments, falling within the scope of the appended claims, and that various alternative embodiments are contemplated. For example, it is envisioned that an insert may be made in accordance with the invention and inserted into a drug container prior to or during filling thereby enabling the use of existing equipment yet providing means to entrap the gas.

What is claimed is:

1. A stopper inside a drug receptacle containing a fluid and a volume of gas therein, said stopper comprising:
    a body that has a driving surface in contact with the fluid in said drug receptacle, said body being movable to displace the fluid therein;
    said driving surface having an upper portion for displacing the volume of gas; and
    said driving surface delivering said displaced fluid, but not the volume of gas, into a lumen that is positioned through said body.

2. The stopper of claim 1 wherein said driving surface is convex.

3. The stopper of claim 2 wherein said driving surface is frusto-conical.

4. The stopper of claim 2 wherein said driving surface is conical.

5. The stopper of claim 1 wherein the body is circular in cross-section.

6. The stopper of claim 1 wherein said driving surface comprises a recess.

7. The stopper of claim 6 wherein an opened end of said lumen is positioned in the recess.

8. The stopper of claim 6 wherein the recess is aligned along the longitudinal axis of the stopper.

9. The stopper of claim 7 wherein said lumen comprises a needle.

10. A stopper inside a drug receptacle containing a fluid and a volume of gas therein, said drug receptacle comprising a lumen having an open end that is positioned in the fluid, said stopper comprising:
    a body that has a driving surface in contact with the fluid in said drug receptacle, said body being movable to displace the fluid therein;
    said driving surface having an upper portion for displacing the volume of gas; and
    said driving surface delivering said displaced fluid, but not the volume of gas, into said lumen.

* * * * *